United States Patent [19]

Commons et al.

[11] Patent Number: 5,439,915
[45] Date of Patent: Aug. 8, 1995

[54] PYRIDO[3,4-B]INDOLE CARBOXAMIDE DERIVATIVES AS SEROTONERGIC AGENTS

[75] Inventors: Thomas J. Commons, Wayne; Christa M. LaClair, Newtown, both of Pa.; Susan Christman, Edison, N.J.

[73] Assignee: American Home Products Corporation, Madison, N.J.

[21] Appl. No.: 326,636

[22] Filed: Oct. 20, 1994

[51] Int. Cl.⁶ .................... A61K 31/44; C07D 471/04
[52] U.S. Cl. ........................................ 514/292; 546/87
[58] Field of Search ..................... 546/84, 87; 514/292

[56] References Cited

U.S. PATENT DOCUMENTS 4,719,211  1/1988  Abou-Gharbia ............... 514/253
4,988,814  1/1991  Abou-Gharbia et al. ........ 544/295

FOREIGN PATENT DOCUMENTS 9311122  6/1993  WIPO.

OTHER PUBLICATIONS

VanderMaelen et al., European Journal of Pharmacology, 129, pp. 123-130, (1986).

*Primary Examiner*—Ceila Chang
*Assistant Examiner*—Evelyn Huang
*Attorney, Agent, or Firm*—Richard K. Jackson

[57] ABSTRACT

The compound of the formula:

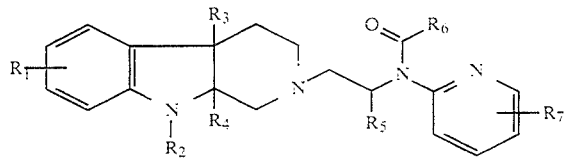

where $R_1$ and $R_7$ are independently hydrogen, fluorine, chlorine, bromine, iodine, trifluoromethyl, cyano, nitro, $CO_2H$, $C_1$–$C_6$ alkyl, $C_2$–$C_{10}$ alkenyl, $C_1$–$C_6$ alkoxy, $C_3$–$C_8$ cycloalkyl, cycloalkylalkyl, $C_3$–$C_8$ cycloalkyloxy, $C_2$–$C_7$ alkylcarbonyl, $C_2$–$C_7$ alkylcarbonyloxy, $C_2$–$C_7$ alkoxycarbonyl, mono or di-alkylaminocarbonyl, tetrazolyl, -OH, -$(CH_2)_{1-6}OH$, -SH, -$NH_2$ or -$(CH_2)_{1-6}NR_8R_9$ where $R_8$ is hydrogen, $C_1$–$C_6$ alkyl, $C_2$–$C_7$ alkylcarbonyl, $C_2$–$C_7$ alkoxycarbonyl and $R_9$ is hydrogen or $C_1$–$C_6$ alkyl; $R_2$ is hydrogen or $C_1$–$C_6$ alkyl; $R_3$ and $R_4$ are hydrogen or taken together with the carbon atoms to which they are attached form a double bond; $R_5$ is hydrogen or $C_1$–$C_6$ alkyl; $R_6$ is $C_1$–$C_{12}$ alkyl, $C_3$ to $C_8$ cycloalkyl, cycloalkylalkyl, or $C_6$ to $C_{12}$ bicyclic or $C_9$ to $C_{14}$ tricyclic alkyl; or a pharmaceutically acceptable salt thereof.

7 Claims, No Drawings

PYRIDO[3,4-B]INDOLE CARBOXAMIDE DERIVATIVES AS SEROTONERGIC AGENTS

BACKGROUND OF INVENTION

The compounds of this invention possess high affinity for the serotonin 5-HT$_{1A}$ receptor and as such are useful as antidepressant and anxiolytic agents for the treatment of a variety of central nervous system disorders such as depression, anxiety, eating disorders, sexual disfunction, addiction and related problems. As an example buspirone (U.S. Pat. No. 3,717,634) is known to display potent affinity for the 5-HT$_{1A}$ serotonin receptor. Buspirone is used extensively for the treatment of anxiety and this anxiolytic activity is believed to be due, at least partially, to its 5-HT$_{1A}$ receptor affinity [VanderMaelen et al., Eut. J. Pharmacol. 1986, 129 (123–130)].

WO 9,311,122-A and U.S. Pat. No. 4,988,814 exemplify 5-HT1A receptor antagonists as derivatives of piperazine.

DESCRIPTION OF THE INVENTION

This invention relates to a series of novel compounds which have activity as serotonergic agents and have the general formula A.

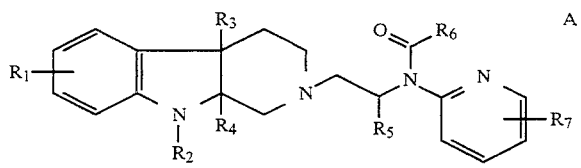

where $R_1$ and $R_7$ are independently hydrogen, fluorine, chlorine, bromine, iodine, trifluoromethyl, cyano, nitro, $CO_2H$, $C_1$–$C_6$ alkyl, $C_2$–$C_{10}$ alkenyl, $C_1$–$C_6$ alkoxy, $C_3$–$C_8$ cycloalkyl, cycloalkylalkyl where the alkyl group is of 1 to 6 carbon atoms and the cycloalkyl group has 3 to 8 carbon atoms, $C_3$–$C_8$ cycloalkyloxy, $C_2$–$C_7$ alkylcarbonyl, $C_2$–$C_7$ alkylcarbonyloxy, $C_2$–$C_7$ alkoxycarbonyl, mono- or di-alkylaminocarbonyl in which each alkyl group, independently, contains 1 to 6 carbon atoms, tetrazolyl, -OH, -(CH$_2$)$_{1-6}$OH, -SH, -NH$_2$ or -(CH$_2$)$_{1-6}$NR$_8$R$_9$ where $R_8$ is hydrogen, $C_1$–$C_6$ alkyl, $C_2$–$C_7$ alkylcarbonyl, $C_2$–$C_7$ alkoxycarbonyl and $R_9$ is hydrogen or $C_1$–$C_6$ alkyl;

$R_2$ is hydrogen or $C_1$–$C_6$ alkyl;

$R_3$ and $R_4$ are hydrogen or taken together with the carbon atoms to which they are attached form a double bond;

$R_5$ is hydrogen or $C_1$–$C_6$ alkyl;

$R_6$ is $C_1$–$C_{12}$ alkyl, $C_3$ to $C_8$ cycloalkyl, cycloalkylalkyl where the alkyl group is of 1 to 6 carbon atoms and the cycloalkyl group has 3 to 8 carbon atoms, or $C_6$ to $C_{12}$ bicyclic or $C_9$ to $C_{14}$ tricyclic alkyl;

or a pharmaceutically acceptable salt thereof.

Of these compounds, a preferred group from the viewpoint of facile production and economic considerations, are those in which $R_1$ and $R_7$, independently, represent hydrogen, fluorine, chlorine, bromine, trifluoromethyl, $CO_2H$, $C_1$–$C_3$ alkyl, $C_1$–$C_3$ alkoxy, $C_2$–$C_4$ alkoxycarbonyl, mono- or dialkylaminocarbonyl in which each alkyl group, independently, contains 1 to 6 carbon atoms, -OH, -NH$_2$ or -(CH$_2$)$_{1-3}$NR$_8$R$_9$ where $R_8$ is hydrogen or $C_1$–$C_3$ alkyl and $R_9$ is hydrogen or $C_1$–$C_3$ alkyl; $R_2$ is H or $C_1$–$C_3$ alkyl; $R_3$ and $R_4$ are hydrogen or taken together with the carbon atoms to which they are attached form a double bond; and $R_5$ is hydrogen or $C_{1-3}$ alkyl; and $R_6$ is $C_1$–$C_3$ alkyl, $C_5$–$C_8$ cycloalkyl or $C_6$ to $C_{12}$ bicyclic or $C_9$ to $C_{14}$ tricyclic alkyl; or a pharmaceutically acceptable salt thereof.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids. Where the compounds of this invention contain acidic substituents such as the carboxylic acid group, salts may be formed with pharmaceutically acceptable bases to form alkali metal (such as Na, K or Li), alkaline earth metal (such as Ca or Mg), the ammonium or mono- or dialkylamine salts, the alkyl portion of said amine salts containing 1 to 6 carbon atoms.

The compounds of this invention possess one or three chiral centers depending on the identity of $R_3$ and $R_4$. Therefore they present diastereoisomers and enantiomers, which may be separated by conventional procedures. In naming the compounds throughout this disclosure and in the appended claims it is to be understood that it is intended to embrace the isomers as their mixtures and in their pure form.

The compounds of this invention are conveniently prepared by the route shown in the following scheme. Specific examples are given in the Experimental Section. These examples are for illustrative purposes only and are not to be construed as limitations for the disclosed invention. Those skilled in the art will be aware of other methods of preparing compounds of this invention. The starting materials or intermediates are available commercially or can be prepared by standard literature procedures.

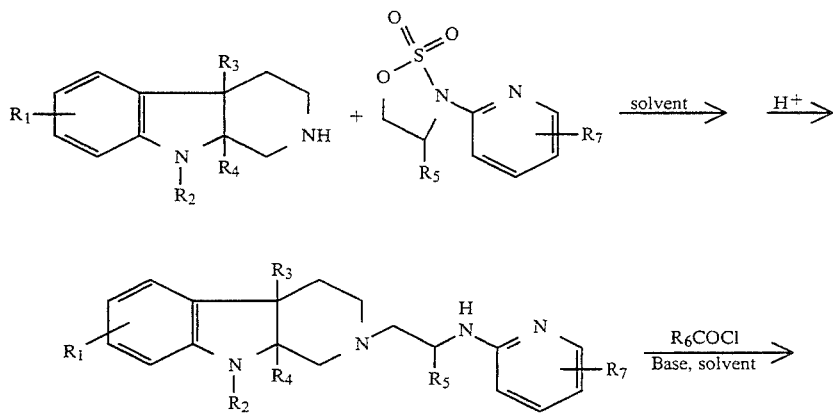

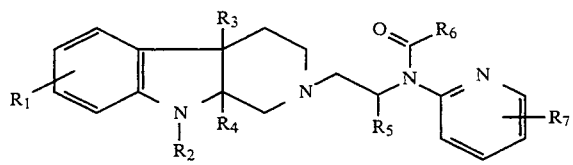

High affinity for the serotonin 5-HT$_{1A}$ receptor for the compounds of this invention was established by testing them in accordance with the standard pharmacological test procedure in which the compound's ability to displace [$^3$H] 8-OHDPAT (dipropylaminotetralin) from the 5-HT$_{1A}$ serotonin receptor was determined following the procedure of Hall et al., J. Neurochem. 44 1685 (1985). This procedure is employed to analogize the properties of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity [VanderMaelen et al., Eur. J. Pharmacol. 1986, 129 (123–130)]. The results of this experimental test procedure are given in the following table:

TABLE

|  | 5-HT$_{1A}$ Binding (IC$_{50}$) |
|---|---|
| Example 1 | 34.9 nM |
| Example 2 | 32.5 nM |
| Example 3 | 78.1 nM |

Hence, the compounds of this invention demonstrated high affinity for the serotonin 5-HT$_{1A}$ receptor subtype, and are therefore useful in the treatment of multi-CNS disorders amenable to treatment with antidepressant and anxiolytic agents.

Based upon this receptor binding data, the compounds of this invention are characterized as anxiolytic and/or antidepressant agents useful in the treatment of depression and in alleviating anxiety. As such, the compounds may be administered neat or with a pharmaceutical carrier to a patient in need thereof. The pharmaceutical carder may be solid or liquid.

Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carder having the necessary compression properties in suitable proportions and compacted in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carders may be used in preparing solutions, suspensions, emulsions, syrups and elixirs. The active ingredient of this invention can be dissolved or suspended in a pharmaceutically acceptable liquid carder such as water, an organic solvent, a mixture of both or pharmaceutically acceptable oils or fat. The liquid carder can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carder can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from depression or anxiety must be subjectively determined by the attending physician. The variables involved include the specific state of anxiety ore depression, and the size, age and response pattern of the patient.

EXAMPLE 1

Cyclohexanecarboxylic acid
[1-methyl-2-(1,3,4,9-tetrahydro-2H-pyrido[3,4-b]indol-2-yl-ethyl-pyridin-2-yl-amide A mixture of 1, 2, 3, 4-tetrahydro-9H-pyrido[3, 4-b]indole (1.7 g, 9.8 mmol) and (R)-4-methyl-3-(pyridin-2-yl)-[1, 2, 3]-oxathiazolidine-2, 2-dioxide (1.90 g, 8.9 mmol) in 30 ml of anhydrous dimethylformamide was stirred under nitrogen at room temperature for two hours. The dimethylformamide was removed under reduced pressure and the residue was dissolved in 15 ml of tetrahydrofuran plus 5 ml of water. Concentrated sulfuric acid (470 µl, 8.9 mmol) was added dropwise and the reaction stirred at room temperature for 30 minutes. Sodium bicarbonate (3.0 g, 35 mmol) is then added and the mixture stirred at room temperature overnight. The reaction was partitioned between ethyl acetate and water. The organic layer was separated.

The aqueous layer was made basic with sodium bicarbonate and then extracted with ethyl acetate. The organic layers were combined, washed two times with water, dried (MgSO$_4$) and the solvent removed under reduced pressure to give 2.68 g (98%) of (R)-[1-methyl-2-(1, 3, 4, 9-tetrahydro-2H-pyrido [3, 4-b]indol-2-yl)-ethyl]-pyridin-2-yl-amine as a light yellow oil, MS [M+HI$^+$307.

Elemental Analysis for C$_{19}$H$_{22}$N$_4$
Calc'd: C, 74.48; H, 7.24; N, 18.29
Found: C, 72.07; H, 7.43; N, 17.21

A solution of cyclohexanecarbonyl chloride (650 gl, 4.9 mmol) in 20 ml of methylene chloride was added under nitrogen dropwise over 10 minutes to a solution of the amine prepared in the preceding step (1.5 g, 4.9 mmol) and triethylamine (680 µl, 4.9 mmol) in 50 ml of methylene chloride at ice bath temperature. After the addition the reaction was stirred at ice bath temperature for approximately four hours and then at room temperature overnight. The reaction was diluted with methylene chloride, extracted two times with 5% NaHCO$_3$, dried (MgSO$_4$) and the solvent removed under reduced pressure to give 1.85 g of a solid yellow foam. Purification of the foam on 200 g of silica gel (230–400 mesh) eluting with 65% ethyl acetate hexane gave 952 mg of a solid yellow foam. This foam was taken up in hot diethyl ether. Upon concentrating and cooling, a solid formed. The solid was collected by filtration and dried under vacuum to give 496 mg (24%) of the title compound as an off white solid, mp 153°–154° C.

Elemental Analysis for C$_{26}$H$_{32}$N$_{40}$
Calc'd: C, 74.97; H, 7.74; N, 13.45
Found: C, 74.94; H, 7.86; N, 13.44

EXAMPLE 2

Adamantane-1-carboxylic acid [1-methyl-2,(1.3.4.9-tetrahydro-2H-pyrido[3.4-blindol-2-yl)-ethyl]-pyridin-2-yl-amide A solution of 1-adamantanecarbonyl chloride (690 mg, 3.4 mmol) in 20 ml of methylene chloride was added under nitrogen dropwise over 10 minutes to a solution of the amine prepared in the first paragraph of Example 1 (1.06 g, 3.4 mmol) and triethylamine (480 µl, 3.4 mmol) in 50 ml of methylene chloride at ice bath temperature. After the addition the reaction was stirred at ice bath temperature for approximately four hours and then at room temperature overnight. By TLC the reaction was not complete. The reaction was cooled to ice bath temperature and an additional 345 mg (1.7 mmol) of 1-adamantanecarbonyl chloride in 5 ml of methylene chloride was added dropwise. After the addition the reaction was stirred at ice bath temperature for approximately four hours and at room temperature overnight. The reaction was diluted with methylene chloride, extracted two times with 5% NaHCO$_3$, dried (MgSO$_4$) and the solvent removed under reduced pressure to give 1.87 g of a solid yellow foam. Purification of the foam on 200 g of silica gel (230–400 mesh) eluting with 50% ethyl acetate—methylene chloride gave 1.33 g of a solid yellow foam. The foam was dissolved in diethyl ether and one equivalent of ethereal HCl was added. The solid formed was collected by filtration and dried under vacuum to give 1.01 g of the title compound as a yellow solid, hydrochloride, hemihydrate, 0.11 diethyl etherate, melting range 165°–190° C.

Elemental Analysis for C$_{30}$H$_{36}$N$_4$O·HCl·0.5 H$_2$O·0.11 C$_4$H$_{10}$O
Calc'd: C, 70.00; H, 7.55; N, 10.73
Found: C, 69.70; H, 7.56; N, 10.68

EXAMPLE 3

Cyclohexanecarboxylic acid [1-methyl-2-(9-methyl-1,3,4,9-tetrahydro-2H-pyrido[3,4-blindol-2-yl)-ethyl]-pyridin-2-yl amide A solution of benzyl chloroformate (8.3 ml, 58 mmol) in 20 ml of anhydrous tetrahydrofuran was added dropwise under nitrogen to a warm solution of 1, 2, 3, 4,-tetrahydro-9H-pyrido [3, 4-blindole (10.0 g, 58 mmol) and triethylamine (8.1 ml, 58 mmol) in 200 ml of anhydrous tetrahydrofuran. After the addition the reaction was stirred at room temperature for four hours. The solvent was removed under reduced pressure and the residue partitioned between ethyl acetate and 1N HCl. The organic layer was separated, extracted one time with 1N HCl, dried (MgSO$_4$) and the solvent removed under reduced pressure to give 15.7 g of an off-white solid. Recrystallization of the solid from 100 ml of 25% hexane—ethyl acetate gave 4.23 g (24%) of the benzyloxycarbonyl derivative of the starting material as a white solid. Recrystallization of the mother liquors from ethyl acetate-diisopropyl ether gave an additional 5.84 g (33%) of material, mp 102°–104° C.

Elemental Analysis for C$_{19}$H$_{18}$N$_2$O$_2$
Calc'd: C, 74.49; H, 5.92; N, 9.14
Found: C, 74.44; H, 5.96; N, 9.30

Sodium hydride [1.5 g of a 60% oil dispersion, (37 mmol)] was added in portions over fifteen minutes to a solution of the material prepared in the preceding step (9.5 g, 31 mmol) in 100 ml of anhydrous dimethylformamide under nitrogen at room temperature. After the addition was complete the reaction was stirred for three hours. Methyl iodide (5.8 nil, 93 mmol) was then added and the reaction stirred at room temperature overnight. The reaction was quenched by the slow addition of 1N HCl. The reaction was then partitioned between 1N HCl and ethyl acetate. The organic layer was separated, washed three times with water, dried (MgSO$_4$) and the solvent removed under reduced pressure to give 10.4 g of a light yellow solid. Recrystallization of the solid from 100 ml of 20% ethyl acetate—diisopropyl ether gave 7.59 g (76%) of the 9-methyl derivative of the starting material as a white solid, mp 100°–101° C.

Elemental Analysis for C$_{20}$H$_{20}$N$_2$O$_2$
Calc'd: C, 74.97; H, 6.29; N, 8.79
Found: C, 74.95; H, 6.30; N, 8.77

A mixture of the material prepared in the preceding step (4.0 g, 12 mmol) and 500 mg of 10% Pd/C in 40 ml of ethyl acetate was hydrogenated at room temperature and 40 psi for 5.5 hours. The catalyst was removed by filtration through celite and then rinsed thoroughly with ethanol and then dimethylformamide. The flitrate was concentrated under reduced pressure to give 2.39 g of an oil. The oil was dissolved in 15 ml of ethanol and then 10 ml of 1N ethereal HCl was added. A solid formed which was collected by filtration, rinsed with diethyl ether and dried under high vacuum to give 2.23 g (80%) of 9-methyl-1, 2, 3, 4,-tetrahydro-9H-pyrido [3, 4-b]indole as the hydrochloride salt, mp >250° C.

Elemental Analysis for C$_{12}$H$_{15}$ClN$_2$
Calc'd: C, 64.71; H, 6.79; N, 12.58
Found: C, 64.50; H, 6.73; N, 12.51

The material prepared in the preceding paragraph (1.0 g, 4.7 mmol) was dissolved in methylene chloride and converted to its free base by treatment with 5%

NaHCO$_3$. The organic layer was separated, dried (MgSO$_4$) and the solvent removed under reduced pressure. The residue was dissolved in 20 ml of acetonitrile and (R)-4-methyl-3-(pyridin-2-yl)-[1, 2, 3]-oxathiazolidine-2, 2-dioxide (1.0 g, 4.7 mmol) was then added and the reaction stirred under nitrogen at room temperature for two hours. Concentrated sulfuric acid (250 ml, 4.7 mmol) was added dropwise and the reaction stirred at room temperature for 30 minutes. Sodium bicarbonate (1.6 g, 19 mmol) and 10 ml of water were added and the reaction stirred at room temperature overnight. The reaction was partitioned between water and methylene chloride. The organic layer was separated, dried (MgSO$_4$) and the solvent removed under reduced pressure to give 1.01 g of a yellow oil. Purification of the oil on 100 g of silica gel (230-400 mesh) eluting with 5% methanol'methylene chloride gave 738 mg (49%) of (R)-[1-methyl-2-(9-methyl-1,3, 4,9-tetrahydro-2H-pyrido[3,4-b]indol-2-yl)-ethyl]-pyridin-2-yl-amine as a yellow oil, MS m/e 320 M+.

A solution of cyclohexanecarbonyl chloride (290 μl, 2.1 mmol) in 5 ml of methylene chloride was added under nitrogen dropwise over 10 minutes to a solution of the amine prepared in the preceding step (686 mg, 2.1 mmol) and triethylamine (300 μl, 2.1 mmol) in 10 ml of methylene chloride at ice batch temperature. After the addition the reaction was stirred at ice bath temperature for approximately four hours and then at room temperature overnight. The reaction was diluted with methylene chloride, extracted two times with 5% NaHCO$_3$, dried (MgSO$_4$) and the solvent removed under reduced pressure to give 933 mg of a yellow oil. Purification of the oil on 140 g of silica gel (230-400 mesh) eluting with 30% to 50% ethyl acetatehexane gave 796 mg of a solid white foam. The foam was dissolved in 10 ml of diethyl ether and 1.7 ml of 1N ethereal HCl was added. The solid formed was collected by filtration, rinsed with diethyl ether and dried under high vacuum to give 689 mg (66%) of the title compound as a light yellow solid, hydrochloride, hydrate, 0.1 diethyl etherate, mp 121°-130° C.

Elemental Analysis for $C_{27}H_{34}N_4O \cdot HCl \cdot H_2O \cdot 0.1\ C_4H_{10}O$
Calc'd: C, 66.82; H, 7.78; N, 11.38
Found: C, 67.19; H, 7.70; N, 11.83

What is claimed is:

1. A compound of the formula:

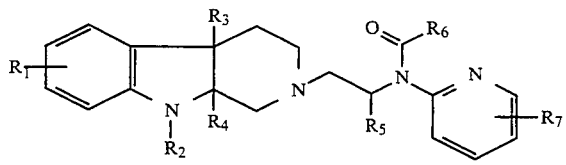

where
R$_1$ and R$_7$ are independently hydrogen, fluorine, chlorine, bromine, iodine, trifluoromethyl, cyano, nitro, CO$_2$H, C$_1$–C$_6$ alkyl, C$_2$–C$_{10}$ alkenyl, C$_1$–C$_6$ alkoxy, C$_3$–C$_8$ cycloalkyl, cycloalkylalkyl where the alkyl group is of 1 to 6 carbon atoms and the cycloalkyl group has 3 to 8 carbon atoms, C$_3$–C$_8$ cycloalkyloxy, C$_2$–C$_7$ alkylcarbonyl, C$_2$–C$_7$ alkylcarbonyloxy, C$_2$–C$_7$ alkoxycarbonyl, mono- or di-alkylaminocarbonyl in which each alkyl group, independently, contains 1 to 6 carbon atoms, tetrazolyl, -OH, -(CH$_2$)$_{1-6}$OH, -SH, -NH$_2$ or -(CH$_2$)$_{1-6}$NR$_8$R$_9$ where R$_8$ is hydrogen, C$_1$–C$_6$ alkyl, C$_2$–C$_7$ alkylcarbonyl, C$_2$–C$_7$ alkoxycarbonyl and R$_9$ is hydrogen or C$_1$–C$_6$ alkyl;

R$_2$ is hydrogen or C$_1$–C$_6$ alkyl;

R$_3$ and R$_4$ are hydrogen or taken together with the carbon atoms to which they are attached form a double bond;

R$_5$ is hydrogen or C$_1$–C$_6$ alkyl;

R$_6$ is C$_1$–C$_{12}$ alkyl, C$_3$ to C$_8$ cycloalkyl, cycloalkylalkyl where the alkyl group is of 1 to 6 carbon atoms and the cycloalkyl group has 3 to 8 carbon atoms, or C$_6$ to C$_{12}$ bicyclic or C$_9$ to C$_{14}$ tricyclic alkyl; or a pharmaceutically acceptable salt thereof.

2. A compound of claim 1 in which R$_1$ and R$_7$, independently, represent hydrogen, fluorine, chlorine, bromine, trifluoromethyl, CO$_2$H, C$_1$–C$_3$ alkyl, C$_1$–C$_3$ alkoxy, C$_2$–C$_4$ alkoxycarbonyl, mono- or di-alkylaminocarbonyl in which each alkyl group, independently, contains 1 to 6 carbon atoms, -OH, -NH$_2$ or -(CH$_2$)$_{1-3}$NR$_8$R$_9$ where R$_8$ is hydrogen or C$_1$–C$_3$ alkyl and R$_9$ is hydrogen or C$_1$–C$_3$ alkyl; R$_2$ is H or C$_1$–C$_3$ alkyl; R$_3$ and R$_4$ are hydrogen or taken together with the carbon atoms to which they are attached form a double bond; and R$_5$ is hydrogen or C$_{1-3}$ alkyl; and R$_6$ is C$_1$–C$_3$ alkyl, C$_5$–C$_8$ cycloalkyl or C$_6$ to C$_{12}$ bicyclic or C$_9$ to C$_{14}$ tricyclic alkyl; or a pharmaceutically acceptable salt thereof.

3. The compound of claim 1 which is cyclohexanecarboxylic acid [1-methyl-2-(1,3,4,9-tetrahydro-2H-pyrido[3,4-b]indol-2-yl)-ethyl]-pyridin-2-yl-amide; or a pharmaceutically acceptable salt thereof.

4. The compound of claim 1 which is adamantane-1-carboxylic acid [1-methyl-2-(1,3,4,9-tetrahydro-2H-pyrido[3,4-b]indol-2-yl)-ethyl]-pyridin-2-yl-amide; or a pharmaceutically acceptable salt thereof.

5. The compound of claim 1 which is cyclohexanecarboxylic acid [1-methyl-2-(9-methyl-1,3,4,9-tetrahydro-2H-pyrido[3,4-b]indol-2-yl]-ethyl]-pyridin-2-yl-amide; or a pharmaceutically acceptable salt thereof.

6. A pharmaceutical composition of matter comprising anxiolytically effective amount of a compound of the formula:

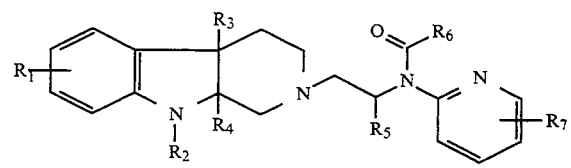

where and R$_7$ are independently hydrogen, fluorine, chlorine, bromine, iodine, trifluoromethyl, cyano, nitro, CO$_2$H, C$_1$–C$_6$ alkyl, C$_2$–C$_{10}$ alkenyl, C$_1$–C$_6$ alkoxy, C$_3$–C$_8$ cycloalkyl, cycloalkylalkyl where the alkyl group is of 1 to 6 carbon atoms and the cycloalkyl group has 3 to 8 carbon atoms, C$_3$–C$_8$ cycloalkyloxy, C$_2$–C$_7$ alkylcarbonyl, C$_2$–C$_7$ alkylcarbonyloxy, C$_2$–C$_7$ alkoxycarbonyl, mono- or di-alkylaminocarbonyl in which each alkyl group, independently, contains 1 to 6 carbon atoms, tetrazolyl, -OH, -(CH$_2$)$_{1-6}$OH, -SH, -NH$_2$ or -(CH$_2$)$_{1-6}$NR$_8$R$_9$ where R$_8$ is hydrogen, C$_1$–C$_6$ alkyl, C$_2$–C$_7$ alkylcarbonyl, C$_2$–C$_7$ alkoxycarbonyl and R$_9$ is hydrogen or C$_1$–C$_6$ alkyl;

R$_2$ is hydrogen or C$_1$–C$_6$ alkyl;

R$_3$ and R$_4$ are hydrogen or taken together with the carbon atoms to which they are attached form a double bond;

$R_5$ is hydrogen or $C_1$–$C_6$ alkyl;

$R_6$ is $C_1$–$C_{12}$ alkyl, $C_3$ to $C_8$ cycloalkyl, cycloalkylalkyl where the alkyl group is of 1 to 6 carbon atoms and the cycloalkyl group has 3 to 8 carbon atoms, or $C_6$ to $C_{12}$ bicyclic or $C_9$ to $C_{14}$ tricyclic alkyl;

or a pharmaceutically acceptable salt thereof; and a pharmaceutically acceptable carrier therefor.

7. A method for relieving the symptoms of anxiety which comprises administering to a mammal in need thereof, orally or parenterally, a compound of the formula:

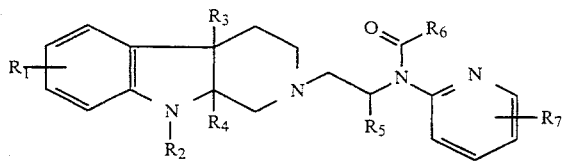

where $R_1$ and $R_7$ are independently hydrogen, fluorine, chlorine, bromine, iodine, trifluoromethyl, cyano, nitro, $CO_2H$, $C_1$–$C_6$ alkyl, $C_2$–$C_{10}$ alkenyl, $C_1$–$C_6$ alkoxy, $C_3$–$C_8$ cycloalkyl, cycloalkylalkyl where the alkyl group is of 1 to 6 carbon atoms and the cycloalkyl group has 3 to 8 carbon atoms, $C_3$–$C_8$ cycloalkyloxy, $C_2$–$C_7$ alkylcarbonyl, $C_2$–$C_7$ alkylcarbonyloxy, $C_2$–$C_7$ alkoxycarbonyl, mono- or di-alkylaminocarbonyl in which each alkyl group, independently, contains 1 to 6 carbon atoms, tetrazolyl, -OH, -$(CH_2)_{1-6}$OH, -SH, -$NH_2$ or -$(CH_2)_{1-6}NR_8R_9$ where $R_8$ is hydrogen, $C_1$–$C_6$ alkyl, $C_2$–$C_7$ alkylcarbonyl, $C_2$–$C_7$ alkoxycarbonyl and $R_9$ is hydrogen or $C_1$–$C_6$ alkyl;

$R_2$ is hydrogen or $C_1$–$C_6$ alkyl;

$R_3$ and $R_4$ are hydrogen or taken together with the carbon atoms to which they are attached form a double bond;

$R_5$ is hydrogen or $C_1$–$C_6$ alkyl;

$R_6$ is $C_1$–$C_{12}$ alkyl, $C_3$ to $C_8$ cycloalkyl, cycloalkylalkyl where the alkyl group is of 1 to 6 carbon atoms and the cycloalkyl group has 3 to 8 carbon atoms or $C_6$ to $C_{12}$ bicyclic or $C_9$ to $C_{14}$ tricyclic alkyl;

or a pharmaceutically acceptable salt thereof, in an anxiolytic amount.

* * * * *